United States Patent
Takizawa et al.

(10) Patent No.: US 7,643,157 B2
(45) Date of Patent: Jan. 5, 2010

(54) PHASE SHIFT AMOUNT MEASUREMENT APPARATUS AND TRANSMITTANCE MEASUREMENT APPARATUS

(75) Inventors: Hideo Takizawa, Kanagawa (JP); Koji Miyazaki, Kanagawa (JP); Haruhiko Kusunose, Kanagawa (JP)

(73) Assignee: Lasertec Corporation, Kanagawa (JP)

( * ) Notice: Subject to any disclaimer, the term of this patent is extended or adjusted under 35 U.S.C. 154(b) by 9 days.

(21) Appl. No.: 12/005,882

(22) Filed: Dec. 28, 2007

(65) Prior Publication Data

US 2008/0174786 A1 Jul. 24, 2008

(30) Foreign Application Priority Data

Jan. 4, 2007 (JP) ............................. 2007-000098
Dec. 28, 2007 (JP) ............................. 2007-339148

(51) Int. Cl.
*G01B 9/02* (2006.01)
(52) U.S. Cl. ...................................... 356/520; 356/521
(58) Field of Classification Search ................ 356/488, 356/494, 499, 521, 520
See application file for complete search history.

(56) References Cited

U.S. PATENT DOCUMENTS 5,426,503 A * 6/1995 Kusunose .................... 356/520
6,078,393 A * 6/2000 Oohashi et al. ............. 356/511

FOREIGN PATENT DOCUMENTS

| JP | 11-327119 | 11/1999 |
| JP | 2005-083974 | 3/2005 |

OTHER PUBLICATIONS

Kusunose et al., Development of Phase-shift and Transmittance Metrology System for a 157nm PSMs, 23rd Annual BACUS Symposium on Photomask Technology. Proceedings of the SPIE, vol. 5256, pp. 628-637, Dec. 17, 2003.

* cited by examiner

*Primary Examiner*—Tarifur Chowdhury
*Assistant Examiner*—Jonathan M Hansen
(74) *Attorney, Agent, or Firm*—Carrier, Blackman & Associates, P.C.; Joseph P. Carrier; William D. Blackman

(57) ABSTRACT

A phase shift amount measurement apparatus able to further correctly measure a phase shift amount of a phase shifter, wherein a laterally offset interference image of a phase shift mask is formed by a shearing interferometer, the interference image is captured by a two-dimensional imaging device, an output signal output from each light receiving element of the two-dimensional imaging device is supplied to a signal processing device, the phase shift amount is calculated for each light receiving element, the light receiving area of the light receiving element is very small, therefore the phase shift amount of any light receiving element outputting a peculiar phase amount due to incidence of diffraction light or multi-reflection light is excluded and the phase shift amount is determined based on the phase shift amount found from output signals of the remaining light receiving elements.

17 Claims, 6 Drawing Sheets wavefront of laterally
offset image 3R wavefront of laterally
offset image 3L field of view of
two imaging device field of view of
two imaging device

PHASE SHIFT AMOUNT MEASUREMENT APPARATUS AND TRANSMITTANCE MEASUREMENT APPARATUS

BACKGROUND OF THE INVENTION

1. Field of the Invention

The present invention relates to a phase shift amount measurement apparatus for measuring a phase shift amount of a phase shift mask.

Further, the present invention relates to a transmittance measurement apparatus for measuring the transmittance of a light shielding pattern of a photo-mask.

2. Description of the Related Art

As photo-masks designed to handle the miniaturization of LSIs, half-tone type phase shift masks and Levenson type phase shift masks have been put into practical use. The phase shift masks are designed so as to give a phase difference of $\pi$ or an odd number of times of that to light passing through adjacent pattern elements of a mask pattern. The resolution of the exposed pattern falls along with the deviation from the design value and the quality as a photo-mask is lowered. For this reason, in the production process of a photo-mask, the phase shift amount is an important parameter for securing the quality. The phase shift amount of a phase shift mask is measured by using a phase shift amount measurement apparatus.

In a conventional phase shift amount measurement apparatus, the measurement was carried out by forming a test pattern on a corner portion of a quartz substrate of the photo-mask, measuring the phase shift amount of the test pattern, and estimating the phase shift amount of an actually used mask pattern (real pattern) based on the measurement result. However, along with the miniaturization of photo-masks, the demand for not measurement according to the test pattern, but the measurement of the phase shift amount of the mask pattern used in actual exposure has becomes stronger. Development of a phase shift amount measurement apparatus able to correctly measure the phase shift amount of an actual pattern has been demanded.

As an apparatus for measuring the phase shift amount of a half tone type phase shift mask, an apparatus projecting illumination light toward the phase shift mask to be checked, making the light transmitted from an opening portion of the phase shift mask and light transmitted from a phase shifter to interfere with each other by using a two-beam interferometer, receiving the emitted interference light by a photomultiplier, and measuring the phase shift amount based on an output signal from the photomultiplier is known (see for example Japanese Patent Publication (A) No. 11-327119).

In a case of measuring the phase shift amount of the actual mask of the half-tone type phase shift mask and a Levenson type phase shift mask, there is the inconvenience that when a pattern edge portion of the mask approaches the light measurement region, strong diffraction light generated by the pattern edge portion enters the light measurement region and becomes noise light. In particular, in a conventional phase shift amount measurement apparatus, interference light emitted from an interference optical system is received by the photomultiplier. Therefore, not only the measurement light, but also the multi-reflected light in the optical system and stray light due to aberration of the lenses strike the photomultiplier, so there was a limit to the measurement precision and reliability. Namely, when measuring interference light by using a single light receiving element having a relatively large light receiving area like a photomultiplier, the diffraction light from the pattern edge portion etc., the multi-reflected light, and so on strike the photomultiplier together with the normal measurement light. The light amount value including the amounts of these lights is output from the photomultiplier. Further, the phase amounts and luminances of these undesired external lights greatly differ from the phase amount etc. of the normal measurement light. Accordingly, when measuring the phase shift amount by using the output signal from a photomultiplier, a large error occurs in the measured phase shift amount.

Further, along with the miniaturization of LSIs, there is a strong demand for managing the transmittance of the light shielding pattern forming the actual mask and for development of a transmittance measurement apparatus able to measure the transmittance of the light shielding pattern of an actual mask with a wide dynamic range.

SUMMARY OF THE INVENTION

An object of the present invention is to provide a phase shift amount measurement apparatus able to measure the phase shift amount further correctly without being influenced by the diffraction light etc. from the edge portions of the pattern formed on the mask pattern when measuring the phase shift amount of an actual mask.

Another object of the present invention is to provide a transmittance measurement apparatus for measuring the transmittance of a light shielding pattern from the laterally offset interference image of an actual mask.

According to a first aspect of the present invention, there is provided a phase shift amount measurement apparatus for measuring a phase shift amount as a phase difference between light transmitted through a phase shift portion of a phase shift mask and light transmitted through a non-phase shift portion, said phase shift amount measurement apparatus provided with an illumination light source projecting illumination light toward a mask pattern of the phase shift mask, a shearing interferometer receiving the light emitted from the mask pattern and forming a laterally offset interference image of the mask pattern, a two-dimensional imaging device having a plurality of light receiving elements and capturing the laterally offset interference image of the mask pattern, a focusing optical system for focusing the laterally offset interference image formed by the shearing interferometer on the two-dimensional imaging device, and a signal processing device for receiving output signals of light receiving elements output from the two-dimensional imaging device and calculating the phase shift amount of the mask pattern for each light receiving element of the two-dimensional imaging device.

According to the present invention, the laterally offset interference image of the mask pattern of the phase shift mask is captured by the two-dimensional imaging device. In the present invention, each light receiving element of the two-dimensional imaging device is treated as an independent photodetector, and the phase shift amount is calculated for each light receiving element based on the output signal from each light receiving element. The surface area of the light incident plane of the light receiving element of the two-dimensional imaging device is much smaller than the area of the light incident plane of the photomultiplier. Therefore, even when diffraction light etc. due to the pattern edge strikes part of the light receiving elements and these light receiving elements output a unique phase shift amount, the related light receiving elements can be excluded from the measurement target, therefore it becomes possible to measure a further correct phase shift amount.

According to a second aspect of the present invention, there is provided a transmittance measurement apparatus for measuring the transmittance of a light shielding pattern formed on a photo-mask, said transmittance measurement apparatus provided with an illumination light source projecting illumination light toward a mask pattern of the phase shift mask, a shearing interferometer receiving the light emitted from the mask pattern and forming a laterally offset interference image of the mask pattern, a two-dimensional imaging device having a plurality of light receiving elements and capturing the laterally offset interference image of the mask pattern, a focusing optical system for focusing the laterally offset interference image formed by the shearing interferometer on the two-dimensional imaging device, a phase modulating means for modulating the phase of said laterally offset interference image over one period, and a signal processing device for receiving output signals of light receiving elements output from said two-dimensional imaging device, calculating an amplitude of phase modulation data of light receiving elements included in a first measurement area in which the image of the light shielding pattern of the captured laterally offset interference image is formed and the amplitude of phase modulation data of light receiving elements included in a second measurement area in which a light shielding pattern is not formed, and calculating the transmittance of the light shielding pattern based on a ratio of amplitudes of phase modulation data of the first measurement area and the second measurement area and a ratio of numbers of light receiving elements included in measurement areas.

According to a third aspect of the present invention, there is provided a phase shift amount measurement method for measuring a phase shift amount as a phase difference between light transmitted through a phase shift portion of a phase shift mask and light transmitted through a non-phase shift portion, said phase shift amount measurement method comprising a step of forming a laterally offset interference image of a mask pattern of the phase shift mask, a step of capturing the formed laterally offset interference image by a two-dimensional imaging device having a plurality of light receiving elements, and a step of calculating the phase shift amount of the mask pattern for each light receiving element of the two-dimensional imaging device.

According to a fourth aspect of the present invention, there is provided a transmittance measurement method for measuring a transmittance of a light shielding pattern formed on a photo-mask, said transmittance measurement method comprising a step of forming a laterally offset interference image of a mask pattern of a photo-mask, a step of capturing the laterally offset interference image by a two-dimensional imaging device having a plurality of light receiving elements, a step of modulating of phase of said laterally offset interference image over one period, a step of defining a first measurement area included in the image of the light shielding pattern and a second measurement area where a light shielding pattern is not formed in the laterally offset interference image, a step of calculating the amplitude of phase modulation data of light receiving elements included in the first measurement area and the amplitude of phase modulation data of light receiving elements included in the second measurement area in which a light shielding pattern is not formed, and a step of calculating the transmittance of the light shielding pattern based on the ratio of the amplitude of the first measurement area and the amplitude of the second measurement area and the ratio of numbers of light receiving elements included in the measurement areas.

In the present invention, the interference image of the actual mask formed by etching is captured by the two-dimensional imaging device, therefore it is possible to measure the transmittance of the light shielding pattern of an actual mask. Further, at the calculation of the transmittance, the numbers of light receiving elements of the image region in which the image of the light shielding pattern is formed and the image region in which a light shielding pattern is not formed can be set with a desired ratio. Therefore, the actual dynamic range is extended by exactly the number of light receiving elements. Even in the case of a light shielding pattern wherein the OD (Optical Density) is about 3 to 4, the transmittance can be correctly measured.

In the present invention, the laterally offset interference image of the mask pattern of the phase shift mask is captured by the two-dimensional imaging device, and the phase shift amount and amplitude are measured for each light receiving element. Therefore the peculiar measurement value can be excluded from the measurement target, and a phase shift amount measurement apparatus not being influenced by undesired diffraction light and multi-reflection light is realized.

BRIEF DESCRIPTION OF THE DRAWINGS

These and other objects and features of the present invention will become clearer from the following description of the preferred embodiments given with reference to the attached drawings, wherein.

DESCRIPTION OF THE PREFERRED EMBODIMENTS

Figure 1:
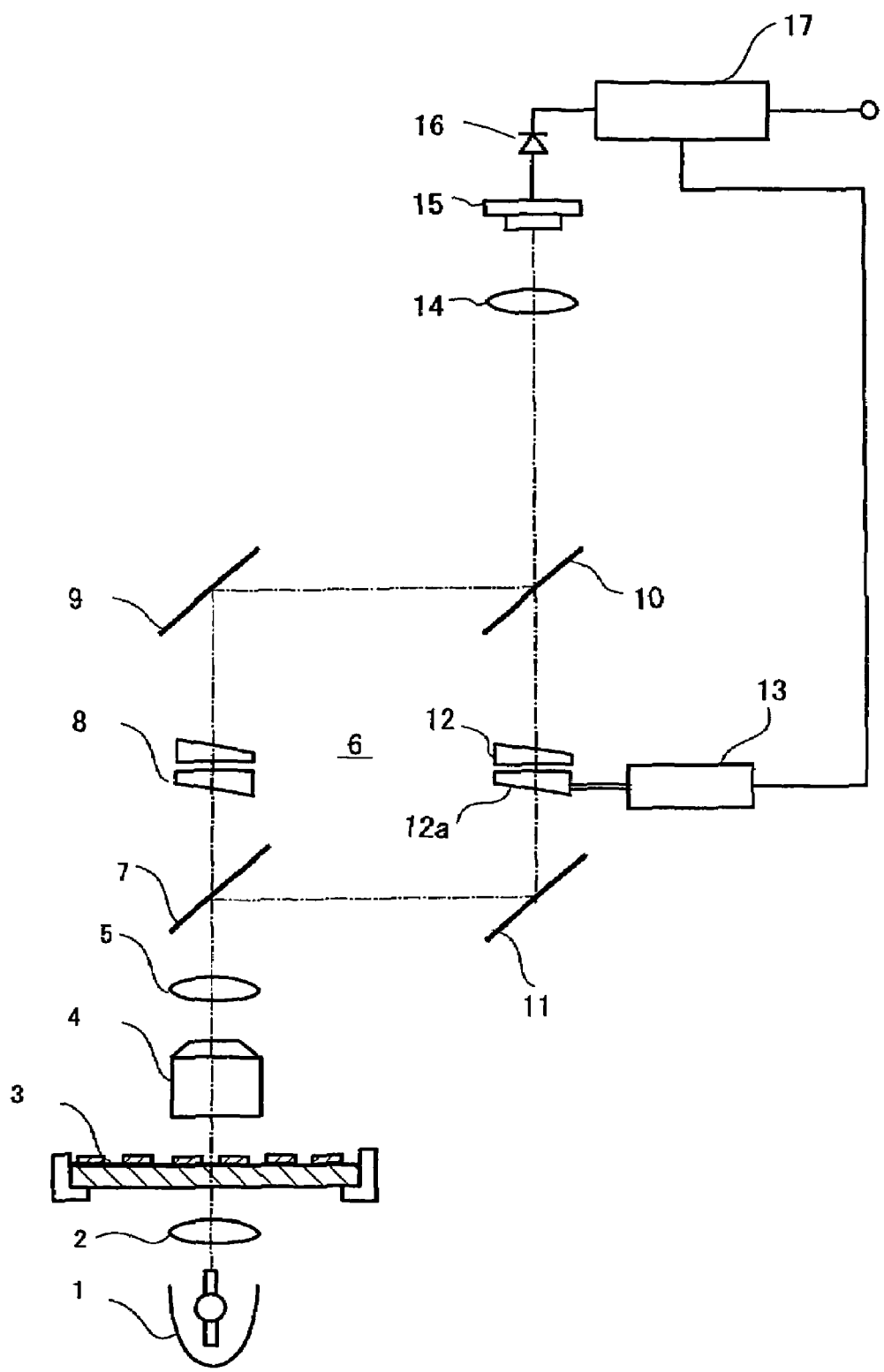
FIG. 1 is a diagram showing an example of a phase shift amount measurement apparatus according to the present invention.

FIG. 1 is a diagram showing an example of a phase shift amount measurement apparatus according to the present invention. Illumination light released from an illumination light source 1 is projected toward the mask pattern of a phase shift mask 3 to be checked which is arranged on an XY stage via a condenser lens 2. As the illumination light source 1, use is made of a light source releasing light having the same wavelength as the wavelength of exposure light which is actually used in an exposure device. For example, when an ArF laser is used in the exposure device, light obtained by splitting light generated from a heavy hydrogen lamp by a prism and having a wavelength of 193.4 nm can be used as the illumination light. The light emitted from the phase shift mask 3 passes through an objective lens 4 and a relay lens 5 and strikes a shearing interferometer 6. This shearing interferometer 6 forms two laterally offset images of the mask pattern, combines the two formed laterally offset images, and outputs a combined laterally offset interference image. As the shearing interferometer, use can be made of Mach-Zehnder interference optical system, Nomarski prism, or other various types of shearing interference optical systems. In the present example, use is made of the Mach-Zehnder interferometer.

The image light striking the Mach-Zehnder interferometer 6 is split by a half mirror 7. One image light passes through a first double wedge prism 8 and total internal reflection mirror 9 and strikes a half mirror 10. The other image light passes through a total internal reflection mirror 11 and second double wedge prism 12 and strikes the half mirror 10. The first and second image light beams form a first and a second laterally offset images, respectively. The first double wedge prism 8 and second double wedge 12 are suitably set and predetermined shearing amount is given to form two laterally offset images. One wedge prism 12a of the second double wedge prism 12 is coupled with a linear motor 13, is moved in a direction perpendicular to the optical axis by the motor, and gives one period's worth of phase modulation with respect to the passing image light.

Two image beams laterally offset by exactly the predetermined shearing amount are combined by the half mirror 10 and strike a focus lens 14. The combined laterally offset interference image is focused onto the two-dimensional imaging device 15 by an imaging lens 14. The two-dimensional imaging device 15 has a plurality of light receiving elements aligned in a two-dimensional array, the image light striking each light receiving element is transformed to an electric signal, and the electric signals of light receiving elements are sequentially read out, pass through an amplifier 16, and are supplied to a signal processing circuit 17. The signal processing circuit 17 comprises Fast Fourier Transformation means which calculate the phase shift amount of the phase shift mask for the light receiving element based on the output signal of the light receiving elements.

Figure 2A:
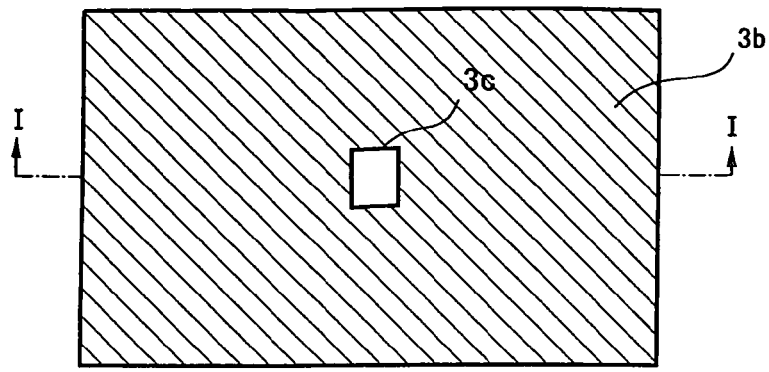
FIGS. 2A to 2D are diagrams showing examples of mask patterns of a phase shift mask.
Figure 2B:
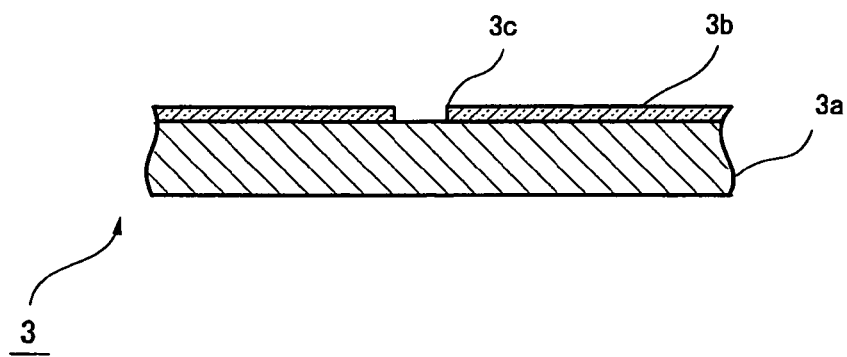
Figure 2C:
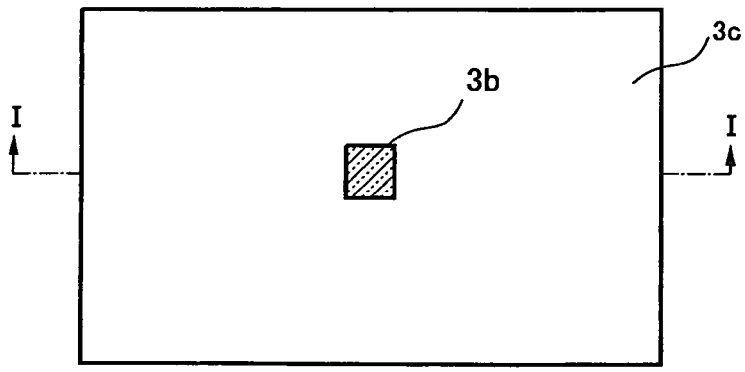
Figure 2D:
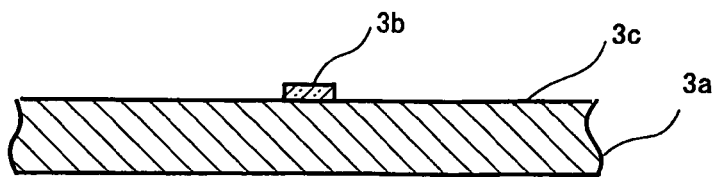

FIGS. 2A to 2D show examples of mask patterns of a phase shift mask to be inspected. The phase shift amount of a half tone type phase shift mask is measured in the present example. FIG. 2A is a plan view, while FIG. 2B is a sectional view taken along a line I-I. The half tone type phase shift mask 3 has a quartz substrate 3a and a half tone film 3b constituting the phase shifter formed on the substrate, and a rectangular opening 3c is formed in the half tone film 3b. In the present specification, a portion where the half tone film is formed is defined as a phase shift portion, and a portion where a half tone film is not formed, but the quartz substrate is exposed (for example, opening 3c) is defined as a non-phase shift portion. The phase shift amount is measured as the phase difference between the beam transmitted through the phase shift portion and the beam transmitted through the non-phase shift portion. Note that, as shown in FIGS. 2C and 2B, a mask pattern where the phase shift portion is formed in a wide non-phase shift portion where a half tone film is not formed is measured in the same way as well.

Note that, the mask patterns shown in FIGS. 2A to 2D are used for convenience of explanation. It is possible to measure the phase shift amounts of various forms of actual masks.

Figure 3:
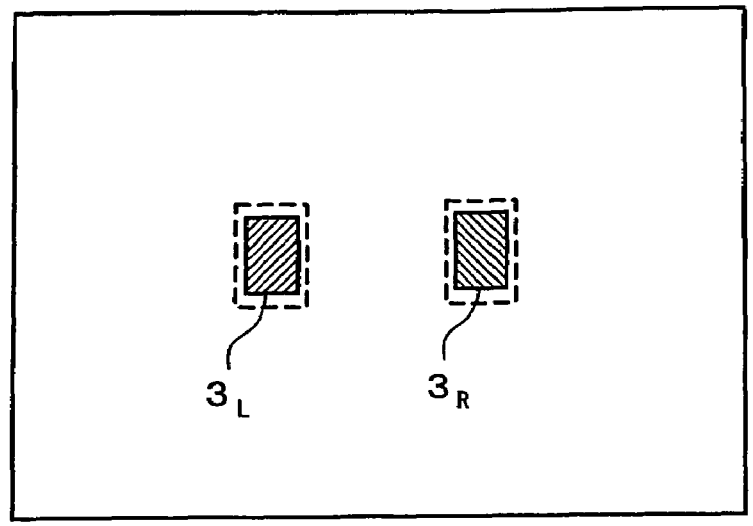
FIG. 3 is a diagram showing two laterally offset pattern images.

For clarifying the explanation, in the present example, an explanation will be given of the method of measurement of the phase shift amount by using the mask pattern shown in FIGS. 2A and 2B as an example. FIG. 3 is a diagram diagrammatically showing two laterally offset interference images of the opening 3c formed on the two-dimensional imaging device 15. By suitably setting the shearing amount of the double wedge prism of the shearing interferometer, the two laterally offset images of the opening 3c of the mask pattern are prevented from being superimposed on each other. Here, an image of the opening formed on the left side on the figure is defined as 3L, and an image of the opening formed on the right side is defined as 3R.

Figure 4:
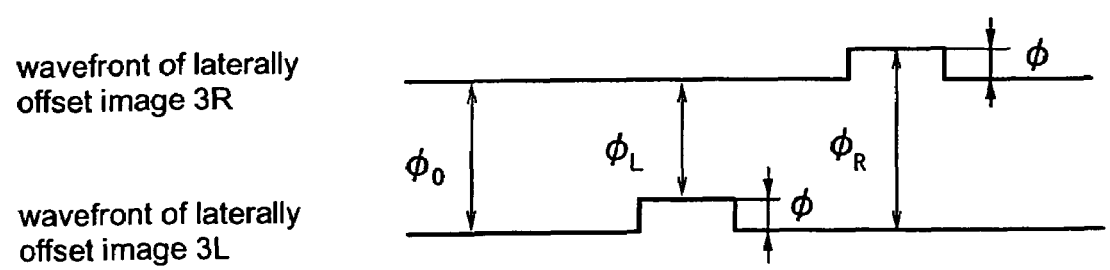
FIG. 4 is a graph showing relationships of wavefronts of pattern images.

FIG. 4 is a diagram diagrammatically showing a relationship of wavefronts of two laterally offset images of the opening 3c formed by the shearing interferometer. In FIG. 4, $\phi o$ indicates a phase difference defined according to an optical path length difference of two beams interfering each other, $\phi L$ indicates the phase difference at the position of the laterally offset interference image 3L, $\phi R$ indicates the phase difference at the position of the laterally offset interference image 3R, and $\phi$ indicates the found phase shift amount of the phase shifter (half tone film). According to the relationship between wavefronts of the two laterally offset images, the following equations stand among $\phi$, $\phi R$, $\phi L$, and $\phi o$.

$$\phi o = \phi L + \phi$$

$$\phi R = \phi o + \phi$$

The phase shift amount $\phi$ of the phase shifter is given according to the following equation:

$$\phi = (\phi R - \phi L)/2$$

Accordingly, the phase shift amount of the phase shifter is found from the phase differences $\phi L$ and $\phi R$ of the two laterally offset images of the mask pattern (opening 3c) included in the laterally offset interference image.

Figure 5:
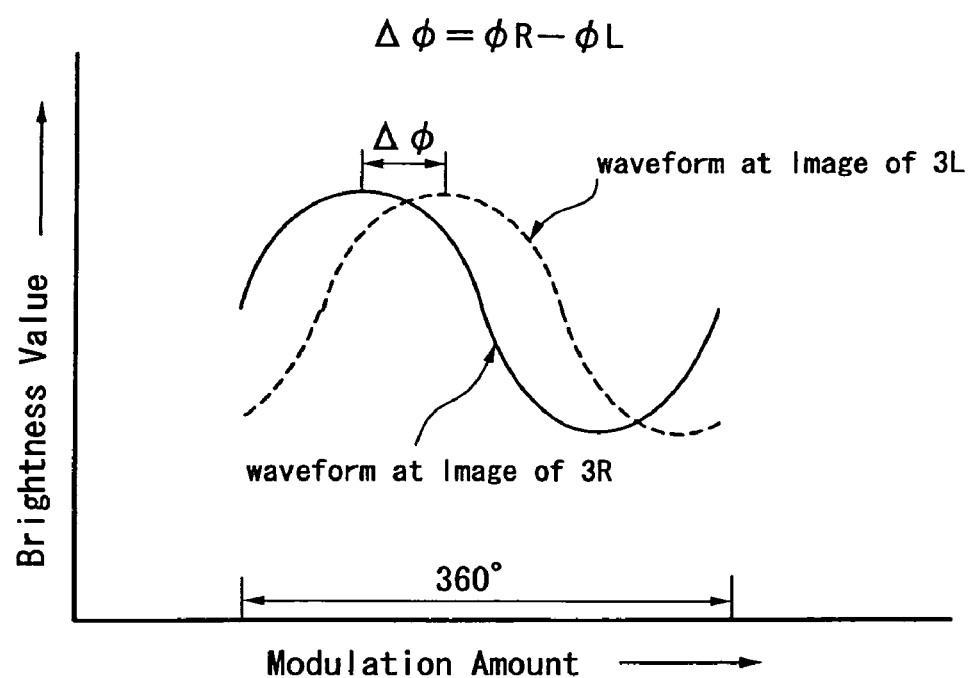
FIG. 5 is a graph showing an example of phase modulation data.

FIG. 5 is a graph showing brightness value change of the interference images 3L and 3R when the phase modulation is carried by moving the wedge prism 12a. By moving the wedge prism 12a by distance one period in the direction perpendicular to the optical axis, phase difference of $2\pi$ is introduced in the image light propagating along one optical path. In FIG. 5, the solid line denotes the change of the output signal (brightness value) from a light receiving element included in the interference image of 3L and the dot line denotes the change of the output signal from a light receiving element included in the interference image of 3R. Here, the phase difference between the peaks of the two line is exactly the phase difference between the interference images 3L and 3R. Such phase difference can be calculated by Fast Fourier Transformation process by use of Fast Fourier Transformation means provided in the signal processing device 17. It is noted that the amount of the phase modulation can be obtained from the position information of the wedge prism 12a. Alternatively, the amount of the phase modulation can be obtained from time information corresponding to the moving speed of the wedge prism. Therefore, the measured phase modulation information and the output signals from the light receiving elements included in the images of 3L and 3R are supplied to the Fast Fourier Transformation means, the phase difference $\Delta\phi$ between the interference images 3L and 3L can be obtained.

Next, the processing routine in the signal processing circuit 17 will be explained.

Step 1

The phase shift mask to be inspected is placed on the XY stage, then a mask pattern suited to measurement of the phase shift amount is selected. Next, the laterally offset interference image of the selected mask pattern is captured and displayed on the monitor. At this time, the XY stage is adjusted, and the two laterally offset images of the mask pattern can be located at the center of the monitor.

Step 2

The operator roughly defines a pixel region which becomes a measurement area for the laterally offset image of the mask pattern displayed on the monitor. When defining the measurement area, as indicated by the broken lines of FIG. 3, a region having a size larger than the laterally offset pattern image may be defined. At this time, a first and a second measurement areas are selected for the two laterally offset pattern images 3R and 3L respectively. As pixel region of the measurement area (light receiving element), for example, a pixel region of 50×50 pixels is defined.

Step 3

One wedge prism 12a of the second double wedge prism 12 is moved by exactly an amount corresponding to the amount of the modulation of the phase of the transmitted light thereof by one period. For example, the relationship between the amount of phase modulation (for example a wedge prism position) and the brightness values (interference intensity) at certain pixels (light receiving elements) in the first and second measuring area is shown in FIG. 5. Therefore, the output signals from the light receiving elements included in the first and second measuring areas are sequentially stored in a memory, and are processed by the high speed Fourier transformation means provided in the signal processing device 17. As the result of this, the relative phase difference between the image 3L and 3R ($\Delta\phi=\phi L-\phi R$) as well as an amplitude I can be obtained. This computation is carried out with respect to all pixels (i,j) included in the first and second measuring areas and the computation results are stored as P1($i,j$) in the memory or hard disk. Simultaneously, amplitude data is calculated as well and stored in the memory as amplitude data I1($i,j$) for each pixel.

Step 4

Next, based on the equations shown below, the phase amount P(i,j) is calculated for each pixel (light receiving element):

$$P(i,j)=\Delta P(i,j)\times(\onehalf)$$

Step 5

Next, for each pixel of the two laterally offset pattern images, any measured peculiar values for the phase amount P(i,j) and amplitude value I(i,j) are excluded from the measurement target. Namely, when diffraction light from a pattern edge portion etc., or multi-reflection light or the like is incident upon the receiving element, the phase amount or amplitude value of the relevant pixel greatly changes from the values of the surrounding pixels. Accordingly, any pixel where either or both of the phase amount and amplitude value greatly change from the values of the surrounding pixels is excluded from the measurement target.

As the method for excluding a pixel having a peculiar value, various methods are used. For example, it is possible to exclude the phase amount of any light receiving element exceeding an upper and a lower predetermined threshold values, and a mean value of phase amounts of remaining light receiving elements is defined as the measured phase amount. Alternatively, it is possible to perform differentiation, compare the differential values with a threshold value, and find the mean value of the phase amounts having measured differential values within the range defined by the predetermined threshold values. Further, it is possible to perform the same processing for the measured amplitude values, exclude the phase amount of any light receiving element having a peculiar amplitude value, and find an average of the amplitude amounts of the remaining light receiving elements as well.

Next, the transmittance measurement according to the present invention will be explained. Along with the miniaturization of photo-masks, the need for managing transmittances of the light shielding patterns of the actual mask and half-tone film has risen. On the other hand, a usual transmittance measurement apparatus has used a measurement beam having a beam diameter of a few millimeters for measurement. Therefore, the measurement of blanks was possible, but it was difficult to measure the transmittance of the light shielding pattern of an actual mask formed on a quartz substrate. Further, as the OD value (Optical Density value) of a light shielding pattern made of metal chromium is about 3 to 4 (transmittance is 0.1 to 0.01%), the resolution of the measurement was low, so there has been the inconvenience that the measured values has deviated from the true transmittance value. Therefore, according to the present invention, the transmittance of the light shielding pattern of the actual mask formed on the substrate is measured by using the above-mentioned measurement apparatus according to the invention.

Figure 6:
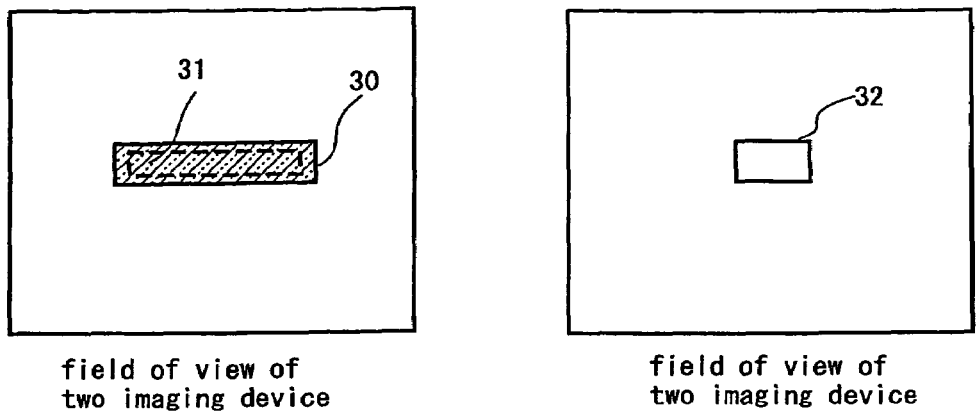
FIG. 6 is a diagram showing a phase shift mask in which a light shielding pattern is formed.

At the measurement of the transmittance, the phase shift amount measurement apparatus shown in FIG. 1 is used as the transmittance measurement apparatus. By use of the phase shift amount measurement apparatus, the image of the light shielding pattern (mask pattern) constituted by the actual mask is captured. For convenience of explanation, the image displayed on a monitor is shown in FIG. 6. In FIG. 6, reference numeral 30 denotes the image of the light shielding pattern made of metal chromium. It is assumed that the surface of the quartz substrate is exposed in the other portion. A region indicated by a broken line in the light shielding pattern 30 is defined as a first measurement area 31. The number of light receiving elements included in the first measurement area 31 is defined as n1. Further, a second measurement area 32 is defined in the region in which the light shielding pattern is removed by etching. The number of light receiving elements included in the second measurement area 32 is defined as n2. The first measurement area and second measurement area are set by the operator while viewing the laterally offset interference image displayed on the monitor or are automatically set by use of an image recognition algorithm.

The amount of the light passing through the light shielding pattern is measured by the light receiving elements included in the first measurement area, while the amount of the light passing through the quartz substrate is measured by the light receiving elements included in the second measurement area. For the numbers of light receiving elements, n1>n2 is set. For example, the number n1 of light receiving elements of the first measurement area is set to 1000 pixels, and the number n2 of the light receiving elements of the second measurement area is set to 5×5 pixels.

Figure 7:
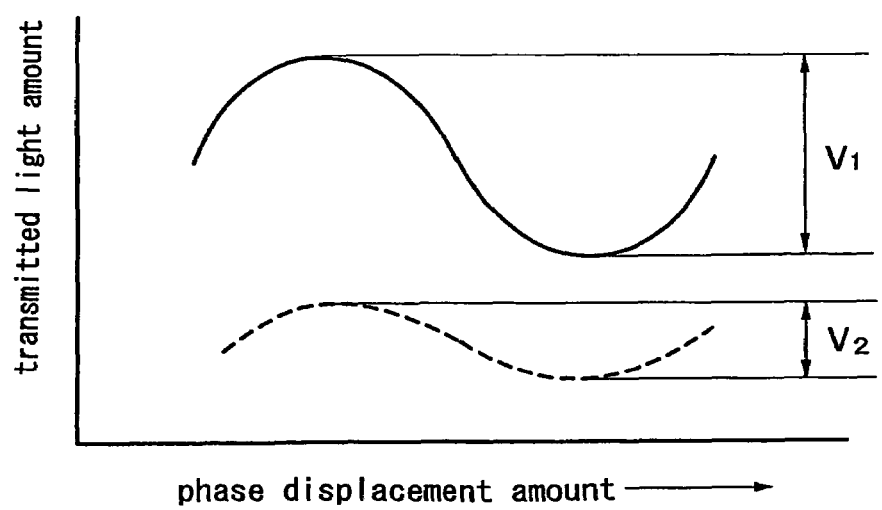
FIG. 7 is a graph showing the relationship between a phase displacement amount and a transmitted light amount at phase modulation.

At the measurement, the wedge prism is moved to modulate the phase by one period and the change of the light amount is measured with respect to the phase modulation of each measurement area. FIG. 7 shows the modulation data output from the light receiving elements of the first and second measurement areas, respectively. In FIG. 7, the solid line indicates the modulation data output from the light receiving elements of the first measurement area, and the broken line indicates the modulation data output from light receiving elements of the second measurement area 32. Further, the amplitude value of the modulation data output from light receiving elements of the first measurement area is defined as $V_1$, and the amplitude value of the modulation data output from light receiving elements of the second measurement area is defined as $V_2$.

The transmittance of the quartz substrate is known in advance, and the transmittance is defined as To. The transmittance T of the light shielding pattern is given by the following equation:

$$T=To(V_1/V_2)\times(n2/n1)$$

As clear from the above equation, the dynamic range of the transmittance measurement increases by exactly the ratio n1/n2 of the numbers of the light receiving elements. As a result of this, the transmittance of the light shielding pattern in which OD is 3 to 4 (transmittance: 0.1 to 0.01) can be measured with a sufficient resolution as well and, at the same time, it becomes possible to measure the transmittance of the light shielding pattern composing the actual mask formed by etching as well.

Figure 8:
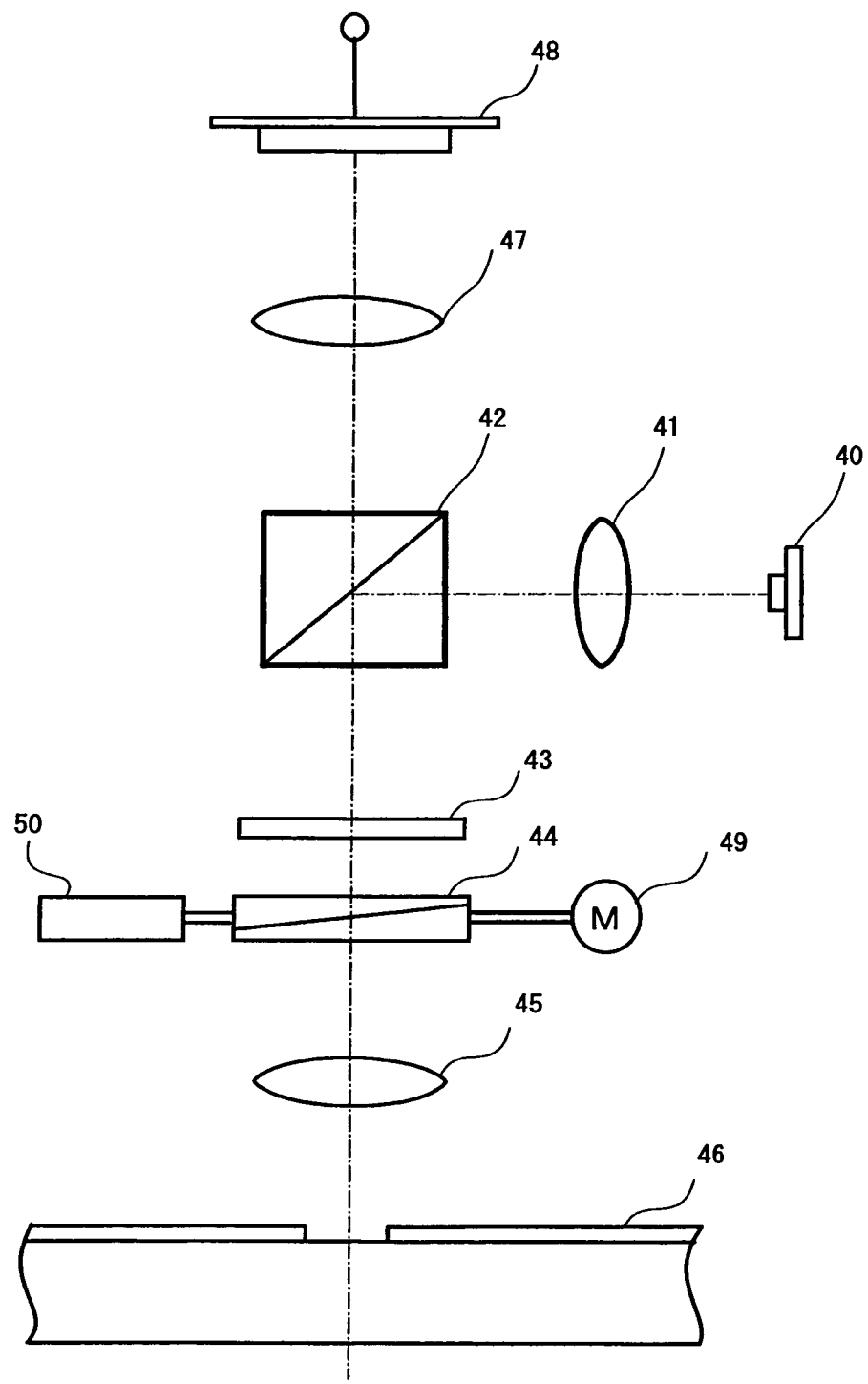
FIG. 8 is a diagram showing a modification of the phase shift amount measurement apparatus and transmittance measurement apparatus according to the present invention.

FIG. 8 is a diagram showing a modification of a phase shift amount measurement apparatus and transmittance measurement apparatus according to the present invention. In the present example, use is made of a Nomarski prism as the shearing interference optical system. For example, a light beam emitted from an illumination light source 40 such as an LED is transformed to spread parallel beams by a collimator lens 41 and is incident upon a polarizing beam splitter 42. The light beam is reflected by the polarizing beam splitter 42 and passes through a λ/4 plate 43 and strike a Nomarski prism 44 acting as the shearing interference optical system. The two optical beams emitted from the Nomarski prism strike a phase shift mask 46 to be measured via an objective lens 45. Reflection beams from the surface of the phase shift mask 46 are condensed by the objective lens 45, strike the Nomarski prism 44 again, and are combined to interference with each other, whereby the two laterally offset interference image is formed. The light beam composing the laterally offset interference images passes through the λ/4 plate 43, beam splitter 42, and imaging lens 47 and is focused onto a two-dimensional imaging device 48.

The Nomarski prism 44 is coupled with a motor 49 and a position detection sensor 50. One period's worth of phase modulation is given by moving the Nomarski prism in a direction perpendicular to the optical axis. The output signal for each light receiving element output from the two-dimensional imaging device is supplied to the signal processing device 19, the signal processing mentioned above is carried out, and the phase shift amount and transmittance of the phase shift mask are output.

While the invention has been described with reference to specific embodiments chosen for purpose of illustration, it should be apparent that numerous modifications could be made thereto by those skilled in the art without departing from the basic concept and scope of the invention.

The invention claimed is:

1. A phase shift amount measurement apparatus for measuring a phase shift amount of a phase shift mask which is a phase difference between light passing through a phase shift portion of a phase shift mask and light passing through a non-phase shift portion, said phase shift amount measurement apparatus comprising:

an illumination light source projecting illumination light toward a mask pattern of the phase shift mask including the phase shift portion and the non-phase shift portion, a shearing interferometer receiving the light emitted from the mask pattern and forming a laterally offset interference image of the mask pattern including two interference pattern images of the mask pattern which are formed by the light passing through the phase shift portion and the light passing through the non-phase shift portion and correspond with each other, a device for modulating a phase of said laterally offset interference image which includes said two interference pattern images over one period, a two-dimensional imaging device having a plurality of light receiving elements and which simultaneously captures said two interference pattern images included in the laterally offset interference image of the mask pattern, wherein said plurality of light receiving elements which simultaneously capture said two interference pattern images form first and second pixel areas, a focusing optical system for focusing the laterally offset interference image formed by the shearing interferometer on the two-dimensional imaging device; and a signal processing device for receiving output signals from the light receiving elements of the first and second pixel areas, calculating phase differences between the two interference pattern images based on phase modulation data over one period outputted from the plurality of light receiving elements capturing said two interference pattern images, and calculating the phase shift amount of the phase shift mask pattern for each light receiving element of the first and second pixel areas based on the calculated phase differences between the two interference pattern images, wherein said signal processing device removes any pixels producing a peculiar amplitude value from measured amplitude values of said light receiving elements and calculates the phase shift amount by use of the output signals from the remaining light receiving elements.

2. A phase shift amount measurement apparatus as set forth in claim 1, wherein said signal processing device comprises a Fast Fourier Transformation device, and said Fast Fourier Transformation device processes the phase modulation data outputted from the light receiving elements included in the first and second measuring areas to output the phase difference information for each light receiving element.

3. A phase shift amount measurement apparatus as set forth in claim 1, wherein shearing interferometer comprises a Mach-Zehnder interferometer, and the Mach-Zehnder interferometer is arranged to receive the transmitted light emitted from the phase shift mask and forms the laterally offset interference image by use of the transmitted light from the mask pattern.

4. A phase shift amount measurement apparatus as set forth in claim 1, wherein said illumination light source comprises an ArF laser.

5. A phase shift amount measurement apparatus as set forth in claim 1, wherein said phase shift mask is a Levenson type phase shift mask or a half-tone type phase shift mask.

6. A phase shift amount measurement apparatus as set forth in claim 1, wherein said first and second pixel areas are operator-selectable pixel areas also within the laterally offset interference image.

7. A phase shift amount measurement apparatus as set forth in claim 1, wherein said peculiar amplitude value is a value which is greatly different from the amplitude values of surrounding pixels.

8. A phase shift amount measurement method for measuring a phase shift amount which is a phase difference between light transmitted through a phase shift portion of a phase shift mask and light transmitted through a non-phase shift portion, said phase shift amount measurement method, comprising the steps of;

projecting illumination light toward a phase shift mask including a phase shift portion and a non-phase shift portion, receiving the light emitted from the phase shift mask and forming a laterally offset interference image of a mask pattern of the phase shift mask which includes two pattern images formed by the light passing through the phase shift portion and the light passing through the non-phase shift portion and which correspond with each other, simultaneously capturing said two pattern images included in the laterally offset image by a two-dimensional imaging device having a plurality of light receiving elements, selecting first and second pixel areas including a plurality of light receiving elements which form said pattern images, respectively, phase modulating the laterally offset interference image over one period so that a phase of said two pattern images is simultaneously modulated over one period to produce phase modulated data, storing, in a memory, the phase modulated data of pixels included in the first and second pixel areas for each pixel, removing any pixels producing a peculiar amplitude value from the first and second pixel areas, calculating a phase difference between the two pattern images based on the phase modulation data of the remaining pixels included in the first and second pixel areas, and calculating the phase shift amount of the phase shift mask based on the calculated phase difference.

9. A phase shift amount measurement method as set forth in claim 8, wherein said the phase modulation data are processed by a Fast Fourier Transformation device to calculate the phase difference.

10. A phase shift amount measurement method as set forth in claim 8, wherein said peculiar amplitude value is a value which is greatly different from the amplitude values of surrounding pixels.

11. A phase shift amount measurement method as set forth in claim 8, wherein said laterally offset interference image is displayed on a monitor for permitting an operator to select the first and second pixel areas which form said pattern images, respectively.

12. A transmittance measurement apparatus for measuring the transmittance of a light shielding pattern formed on a photo-mask, said transmittance measurement apparatus comprising:

an illumination light source projecting illumination light toward a mask pattern of the photo-mask, a shearing interferometer receiving the light emitted from the mask pattern and forming a laterally offset interference image of the mask pattern, a two-dimensional imaging device having a plurality of light receiving elements and capturing the laterally offset interference image of the mask pattern, a focusing optical system for focusing the laterally offset interference image formed by the shearing interferometer on the two-dimensional imaging device, a phase modulating device for modulating the phase of said laterally offset interference image over one period, and a signal processing device for receiving output signals of light receiving elements output from said two-dimensional imaging device, calculating an amplitude of phase modulation data of light receiving elements included in a first measurement area in which the image of the light shielding pattern of the captured laterally offset interference image is formed and an amplitude of phase modulation data of light receiving elements included in a second measurement area in which a light shielding pattern is not formed, and calculating the transmittance of the light shielding pattern based on a ratio of amplitudes of phase modulation data of the first measurement area and the second measurement area and a ratio of numbers of light receiving elements included in the measurement areas.

13. A transmittance measurement apparatus as set forth in claim 12, wherein when transmittance of a substrate of the photo-mask is defined as $T_0$, transmittance of the light shielding pattern is defined as T, the amplitude values of the modulated data output from the light receiving elements of the first and second measurement areas are defined as $V_1$ and $V_2$, and the numbers of the light receiving elements included in the first and second measurement areas are defined as n1 and n2, respectively, said signal processing device calculates the transmittance of the light shielding pattern according to the following equation:

$T=T_0(V_1/V_2)\times(n2/n1)$.

14. A transmittance measurement apparatus as set forth in claim 13, wherein the numbers of the light receiving elements included in the first and second measurement areas n1 and n2 satisfy the relation of n1>n2.

15. A transmittance measurement method for measuring a transmittance of a light shielding pattern formed on a photo-mask, said transmittance measurement method comprising the steps of;

projecting an illumination beam toward the photo-mask to be inspected, forming a laterally offset interference image of a mask pattern of the photo-mask, capturing the laterally offset interference image by a two-dimensional imaging device having a plurality of light receiving elements, phase modulating said laterally offset interference image over one period, defining a first measuring area included in the image of the light shielding pattern and a second measuring area where a light shielding pattern is not formed in the laterally offset interference image, calculating an amplitude of phase modulation data of light receiving elements included in the first measuring area and an amplitude of phase modulation data of light receiving elements included in the second measuring area in which a light shielding pattern is not formed, and calculating a transmittance of the light shielding pattern based on a ratio of the amplitude of the first measurement area and the amplitude of the second measurement area and a ratio of numbers of light receiving elements included in the measurement areas.

16. A transmittance measurement method as set forth in claim 15, wherein when transmittance of a substrate of the photo-mask is defined as $T_0$, transmittance of the light shielding pattern is defined as T, the amplitude values of the modulated data output from the light receiving elements of the first and second measurement area are defined as $V_1$ and $V_2$, and the numbers of the light receiving elements included in the first and second measurement areas are defined as n1 and n2, respectively, said transmittance of the light shielding pattern is calculated according to the following equation:

$T=T_0(V_1/V_2)\times(n2/n1)$.

17. A transmittance measurement method as set forth in claim 16, wherein the numbers of the light receiving elements included in the first and second measurement areas n1 and n2 satisfy the relation of n1>n2.

* * * * *

UNITED STATES PATENT AND TRADEMARK OFFICE
CERTIFICATE OF CORRECTION

PATENT NO. : 7,643,157 B2
APPLICATION NO. : 12/005882
DATED : January 5, 2010
INVENTOR(S) : Takizawa et al.

It is certified that error appears in the above-identified patent and that said Letters Patent is hereby corrected as shown below:

Title page:
In section (56), References cited, further under "OTHER PUBLICATIONS", change "for a 157nm" to --for 157-nm--.
After "*Assistant Examiner—*" change "Jonathan M Hansen" to --Jonathan M. Hansen--.

In the Specification:
Column 1:
Line 13, change "light shielding pattern" to --light-shielding pattern--.
Line 16, change "half-tone type" to --halftone-type--; change "Levenson type" to --Levenson-type--.
Line 35, change "not measurement" to --not measuring--.
Line 36, change "the measurement of" to --for measuring instead according to--.
Line 37, change "exposure has becomes" to --exposure, has become--.
Line 42, change "half tone type" to --halftone-type--.
Line 52, change "half-tone type" to --halftone-type--; change "a Levenson" to --a Levenson- --.
Line 63, change "there was a limit" to --there is a limit--.
Line 65, change "light receiving element" to --light-receiving element--.
Line 66, change "light receiving area" to --light-receiving area--.

Column 2:
Line 1, change "and so on strike" to --and so on, strike--.
Lines 11-12 and line 14, change "light shielding pattern" to --light-shielding pattern--.
Line 21, change "amount further correctly" to --amount more correctly--.
Line 27, change "light shielding pattern" to --light-shielding pattern--.
Line 40, change "light receiving elements" to --light-receiving elements--.
Line 44, change "signal processing device" to --signal-processing device--.
Line 45, change "light receiving elements" to --light-receiving elements--.
Line 47, change "each light receiv-" to --each light-receiv- --.
Line 52, line 55, line 56, and line 57, change "light receiving element" to --light-receiving element--.

Signed and Sealed this

Twentieth Day of July, 2010

David J. Kappos
*Director of the United States Patent and Trademark Office*

CERTIFICATE OF CORRECTION (continued)
U.S. Pat. No. 7,643,157 B2

Column 2 (continued):
    Line 61, change "light receiving elements" (both occurrences) to --light-receiving elements--.
    Line 62, change "related light receiving" to --related light-receiving--.
    Line 64, change "a further correct" to --a more correct--.

Column 3:
    Line 1, change "light shielding pattern" to --light-shielding pattern--.
    Line 8, change "light receiving elements" to --light-receiving elements--.
    Line 12, change "phase modulating means" to --phase-modulating means--.
    Line 14, change "signal processing device" to --signal-processing device--.
    Line 15, change "light receiving elements" to --light-receiving elements--.
    Line 17, change "light receiving ele-" to --light-receiving ele- --.
    Line 19, change "light shielding pattern" to --light-shielding pattern--.
    Line 21, change "light receiving elements" to --light-receiving elements--.
    Line 22 and lines 23-24, change "light shielding pattern" to --light-shielding pattern--.
    Lines 26-27 and line 37, change "light receiving elements" to --light-receiving elements--.
    Line 39, change "light receiving element" to --light-receiving element--.
    Line 43, change "light shielding pattern" to --light-shielding pattern--.
    Line 48, change "light receiving elements" to --light-receiving elements--.
    Line 51, change "image of the light shielding" to --image of the light-shielding--.
    Line 52, change "where a light shield-" to --where a light-shield- --.
    Line 55 and line 57, change "light receiving elements" to --light-receiving elements--.
    Line 58, change "light shielding pattern" to --light-shielding pattern--.
    Line 59, change "of the light shield-" to --of the light-shield- --.
    Line 62, change "light receiving elements" to --light-receiving elements--.
    Line 66, change "device, therefore it is" to --device; therefore, it is--.
    Line 67, change "light shielding pattern" to --light-shielding pattern--.

Column 4:
    Line 2, change "light receiving elements" to --light-receiving elements--.
    Line 3 and line 4, change "light shielding pattern" to --light-shielding pattern--.
    Line 6, change "light receiving elements" to --light-receiving elements--.
    Line 7, change "light shielding pattern" to --light-shielding pattern--.
    Line 13, change "each light receiving" to --each light-receiving--.
    Line 14, change "Therefore the peculiar" to --Therefore, the peculiar--.
    Line 38, change "light shielding pattern" to --light-shielding pattern--.

Column 5:
    Line 11, change "form a first and a second" to --form first and second--.
    Line 13, change "double wedge 12" to --double wedge prism 12--.
    Line 14, change "predetermined" to --a predetermined--.
    Line 25, change "of light receiving" to --of light-receiving--.
    Line 27, change "each light receiving" to --each light-receiving--.
    Line 28, change "signals of light receiving" to --signals of light-receiving--.
    Line 30, change "signal processing circuit 17. The signal" to --signal-processing circuit 17. The signal- --.
    Line 34, change "light receiving element" to --light-receiving element--.
    Line 35, change "light receiving elements" to --light-receiving elements--.

Column 5 (continued):
    Line 37, change "amount of a half" to --amount of a half- --.
    Line 38, change "tone type" to --tone-type--.
    Line 40, change "half tone type" to --halftone-type--.
    Line 41 and line 43, change "half tone film 3*b*" to --halftone film 3*b*--.
    Line 44, change "half tone film is" to --halftone film is--.
    Line 45, change "where a half" to --where a half- --.
    Line 53, change "half tone film" to --halftone film--.

Column 6:
    Line 13, change "(half tone film)" to --(halftone film)--.
    Line 30, change "carried by" to --carried out by--.
    Line 31, change "by distance one" to --by a distance of one--.
    Line 35 and lines 37-38, change "light receiving element" to --light-receiving element--.
    Line 39, change "peaks of the two line" to --peaks of the two lines--.
    Lines 49-50, change "light receiving elements" to --light-receiving elements--.
    Line 52, change "images 3L and 3L can" to --images 3L and 3R can--.

Column 7:
    Line 3, change "time, a first and a second" to --time, first and second--.
    Line 6, change "(light receiving element)" to --(light-receiving element)--.
    Line 15, change "(light receiving elements)" to --(light-receiving elements)--.
    Line 16, change "measuring area is" to --measuring areas is--.
    Line 17, change "light receiving elements" to --light-receiving elements--.
    Line 19, change "high speed Fourier" to --high-speed Fourier--.
    Line 20, change "signal processing device" to --signal-processing device--.
    Line 26, change "amplitude data is" to --amplitude data are--.
    Lines 31-32, change "(light receiving element)" to --(light-receiving element)--.
    Line 49, change "light receiving element" to --light-receiving element--.
    Lines 51-52, change "light receiving elements" to --light-receiving elements--.
    Line 59, change "light receiving element" to --light-receiving element--.
    Line 61, change "light receiving elements" to --light-receiving elements--.
    Line 65, change "light shielding patterns" to --light-shielding patterns--; change "half-tone" to --halftone--.

Column 8:
    Lines 3-4, change "light shielding pattern" to --light-shielding pattern--.
    Line 5, change "a light shield-" to --a light-shield- --.
    Line 9, change "values has deviated" to --values have deviated--.
    Line 11, lines 17-18, lines 21-22, and line 24, change "light shielding pattern" to --light-shielding pattern--.
    Line 26, change "light receiving elements" to --light-receiving elements--.
    Line 28, change "light shielding pattern" to --light-shielding pattern--.
    Line 29, change "light receiving ele-" to --light-receiving ele- --.
    Lines 35-36, change "light shielding pattern" to --light-shielding pattern--.
    Line 36, lines 38-39, line 40, line 41, line 43, line 49, lines 51-52, lines 53-54, lines 55-56, and line 58, change "light receiving elements" to --light-receiving elements--.
    Line 62, change "light shielding pattern" to --light-shielding pattern-.

Column 9:
    Line 1, change "light receiving elements" to --light-receiving elements--.
    Line 2 and lines 5-6, change "light shielding pattern" to --light-shielding pattern--.
    Line 17, change "and strike a" to --and strikes a--.
    Line 23, change "combined to interference" to --combined to interfere--.
    Line 24, change "image is formed" to --images are formed--.
    Line 33, change "light receiving element" to --light-receiving element--.
    Lines 34-35, change "signal processing device" to --signal-processing device--.
In the Claims:
    Line 59, change "and correspond" to --and which correspond--.
    Lines 64 and line 67, change "light receiving elements" to --light-receiving elements--.

Column 10:
    Line 6, change "signal processing device" to --signal-processing device--.
    Line 7 and line 11, change "light receiving elements" to --light-receiving elements--.
    Lines 13-14, change "light receiving element" to --light-receiving element--.
    Line 17, change "signal processing device" to --signal-processing device--.
    Line 19 and line 21, change "light receiving elements" to --light-receiving elements--.
    Line 24, change "signal processing device" to --signal-processing device--.
    Line 27, change "light receiving elements" to --light-receiving elements--.
    Line 29, change "light receiving element" to --light-receiving element--.
    Line 31, change "wherein shearing interferometer" to --wherein the shearing interferometer--.
    Line 41, change "Levenson type" to --Levenson-type--.
    Line 42, change "half-tone type" to --halftone-type--.
    Line 56, change "method, comprising" to --method comprising--.
    Line 57, change "the steps of;" to --the steps of:--.

Column 11:
    Line 3 and line 5, change "light receiving elements" to --light-receiving elements--.
    Line 10 and line 11, change "phase modulated data" to --phase-modulated data--.
    Line 23, change "wherein said the phase" to --wherein said phase--.
    Line 36, change "light shielding pattern" to --light-shielding pattern--.
    Line 45, change "light receiving elements" to --light-receiving elements--.
    Line 50, change "phase modulating device" to --phase-modulating device--.
    Line 52, change "signal processing device" to --signal-processing device--.
    Line 53 and line 55, change "light receiving elements" to --light-receiving elements--.
    Lines 56-57, change "light shielding pattern" to --light-shielding pattern--.
    Line 59, change "light receiving elements" to --light-receiving elements--.
    Lines 60-61 and line 62, change "light shielding pattern" to --light-shielding pattern--.

Column 12:
    Line 2, change "light receiving elements" to --light-receiving elements--.
    Line 6, change "the light shield-" to --the light-shield- --.
    Line 8 and line 10, change "light receiving elements" to --light-receiving elements--.
    Line 12, change "signal processing device" to --signal-processing device--.
    Line 13, change "light shielding pattern" to --light-shielding pattern--.
    Line 18, change "light receiving elements" to --light-receiving elements--.
    Line 22, change "light shielding pattern" to --light-shielding pattern--.
    Line 23, change "transmiftance" to --transmittance--.

CERTIFICATE OF CORRECTION (continued)
U.S. Pat. No. 7,643,157 B2

Column 12 (continued):
    Line 24, change "the steps of;" to --the steps of:--.
    Lines 30-31, change "light receiving elements" to --light-receiving elements--.
    Line 35, change "light shielding pattern and" to --light-shielding pattern and--.
    Line 36, change "light shielding pattern is" to --light-shielding pattern is--.
    Lines 38-39 and line 40-41, change "light receiving elements" to --light-receiving elements--.
    Line 42 and line 43, change "light shielding pattern" to --light-shielding pattern--.
    Line 46, change "light receiving elements" to --light-receiving elements--.
    Line 48, change "transmiftance" to --transmittance--.
    Line 50, change "a light shield-" to --a light-shield- --.
    Line 52, change "light receiving elements" to --light-receiving elements--.
    Line 53, change "measurement area" to --measurement areas--.
    Line 54, change "light receiving elements" to --light-receiving elements--.
    Line 56, change "light shielding pattern" to --light-shielding pattern--.
    Line 59, change "transmiftance" to --transmittance--.
    Line 60, change "light receiving elements" to --light-receiving elements--.